United States Patent
Johnston et al.

(10) Patent No.: US 8,536,384 B2
(45) Date of Patent: *Sep. 17, 2013

(54) RECOVERING ETHANOL SIDEDRAW BY SEPARATING CRUDE PRODUCT FROM HYDROGENATION PROCESS

(75) Inventors: Victor J. Johnston, Houston, TX (US); Radmila Jevtic, Pasadena, TX (US); David Lee, Seabrook, TX (US); Adam Orosco, Houston, TX (US); R. Jay Warner, Houston, TX (US); Heiko Weiner, Pasadena, TX (US); Zhenhua Zhou, Houston, TX (US); Emily Duff, League City, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/456,651

(22) Filed: Apr. 26, 2012

(65) Prior Publication Data

US 2012/0245396 A1    Sep. 27, 2012

Related U.S. Application Data

(63) Continuation-in-part of application No. 13/094,537, filed on Apr. 26, 2011.

(60) Provisional application No. 61/570,604, filed on Dec. 14, 2011, provisional application No. 61/363,109, filed on Jul. 9, 2010.

(51) Int. Cl.
*C07C 29/149* (2006.01)

(52) U.S. Cl.
USPC ........................................................ 568/885

(58) Field of Classification Search
USPC ........................................................ 568/885
See application file for complete search history.

(56) References Cited

U.S. PATENT DOCUMENTS

| | | | |
|---|---|---|---|
| 2,649,407 A | 8/1953 | Harrison et al. | |
| 2,702,783 A | 2/1955 | Harrison et al. | |
| 3,408,267 A | 10/1968 | Miller et al. | |
| 3,445,345 A | 5/1969 | Katzen et al. | |
| 3,478,112 A | 11/1969 | Karl et al. | |
| 3,990,952 A | 11/1976 | Katzen et al. | |
| 4,275,228 A | 6/1981 | Gruffaz et al. | |
| 4,306,942 A | 12/1981 | Brush et al. | |
| 4,308,131 A | 12/1981 | Bannon | |
| 4,317,918 A | 3/1982 | Takano et al. | |
| 4,319,058 A | 3/1982 | Kulprathipanja et al. | |
| 4,379,028 A | 4/1983 | Berg et al. | |
| 4,395,576 A | 7/1983 | Kwantes et al. | |
| 4,398,039 A | 8/1983 | Pesa et al. | |
| 4,421,939 A | 12/1983 | Kiff et al. | |
| 4,422,903 A | 12/1983 | Messick et al. | |
| 4,454,358 A | 6/1984 | Kummer et al. | |
| 4,465,854 A | 8/1984 | Pond et al. | |
| 4,471,136 A | 9/1984 | Larkins et al. | |
| 4,480,115 A | 10/1984 | McGinnis | |
| 4,492,808 A | 1/1985 | Hagen et al. | |
| 4,497,967 A | 2/1985 | Wan | |
| 4,520,213 A | 5/1985 | Victor | |
| 4,541,897 A | 9/1985 | Sommer et al. | |
| 4,626,321 A | 12/1986 | Grethlein et al. | |
| 4,678,543 A | 7/1987 | Houben et al. | |
| 4,692,218 A | 9/1987 | Houben et al. | |
| 4,777,303 A | 10/1988 | Kitson et al. | |
| 4,804,791 A | 2/1989 | Kitson et al. | |
| 4,842,693 A | 6/1989 | Wheldon | |
| 4,961,826 A | 10/1990 | Grethlein et al. | |
| 4,985,572 A | 1/1991 | Kitson et al. | |
| 4,990,655 A | 2/1991 | Kitson et al. | |
| 5,035,776 A | 7/1991 | Knapp | |
| 5,061,671 A | 10/1991 | Kitson et al. | |
| 5,124,004 A | 6/1992 | Grethlein et al. | |
| 5,149,680 A | 9/1992 | Kitson et al. | |
| 5,185,481 A | 2/1993 | Muto et al. | |
| 5,215,902 A | 6/1993 | Tedder | |
| 5,227,141 A | 7/1993 | Kim et al. | |
| 5,233,099 A | 8/1993 | Tabata et al. | |

(Continued)

FOREIGN PATENT DOCUMENTS

CN    201768393       3/2011
EP    0 010 927 A1    5/1980

(Continued)

OTHER PUBLICATIONS

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

(Continued)

*Primary Examiner* — Elvis O Price

(57) ABSTRACT

A process for producing ethanol is disclosed, comprising the steps of hydrogenating acetic acid in a reactor in the presence of a catalyst to form a crude ethanol product, separating at least a portion of the crude ethanol product in a column into a first distillate comprising ethanol and a first residue comprising acetic acid and water, wherein a substantial portion of the water in the crude ethanol product that is fed to the column is removed in the first residue, and separating a portion of the ethanol mixture stream to the second distillation column to yield an ethanol product sidedraw, second residue comprising water and a second distillate comprising ethyl acetate. The water content of the ethanol product sidedraw may be further reduced to yield a stream having reduced water content.

23 Claims, 6 Drawing Sheets

(56) References Cited

U.S. PATENT DOCUMENTS

| | | |
|---|---|---|
| 5,237,108 A | 8/1993 | Marraccini et al. |
| 5,250,271 A | 10/1993 | Horizoe et al. |
| 5,348,625 A | 9/1994 | Berg |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli et al. |
| 5,762,765 A | 6/1998 | Berg |
| 5,770,770 A | 6/1998 | Kim et al. |
| 5,800,681 A | 9/1998 | Berg |
| 5,993,610 A | 11/1999 | Berg |
| 6,121,498 A | 9/2000 | Tustin et al. |
| 6,294,703 B1 | 9/2001 | Hara et al. |
| 6,375,807 B1 | 4/2002 | Nieuwoudt et al. |
| 6,509,180 B1 | 1/2003 | Verser et al. |
| 6,693,213 B1 | 2/2004 | Kolena et al. |
| 6,723,886 B2 | 4/2004 | Allison et al. |
| 6,906,228 B2 | 6/2005 | Fischer et al. |
| 6,927,048 B2 | 8/2005 | Verser et al. |
| 7,297,236 B1 | 11/2007 | Vander Griend et al. |
| 7,399,892 B2 | 7/2008 | Rix et al. |
| 7,507,562 B2 | 3/2009 | Verser et al. |
| 7,553,397 B1 | 6/2009 | Colley et al. |
| 7,572,353 B1 | 8/2009 | Vander et al. |
| 7,594,981 B2 | 9/2009 | Ikeda |
| 7,608,744 B1 | 10/2009 | Johnston et al. |
| 7,732,173 B2 | 6/2010 | Mairal et al. |
| 7,744,727 B2 | 6/2010 | Blum et al. |
| 7,842,844 B2 | 11/2010 | Atkins |
| 2006/0019360 A1 | 1/2006 | Verser et al. |
| 2006/0127999 A1 | 6/2006 | Verser et al. |
| 2007/0270511 A1 | 11/2007 | Melnichuk et al. |
| 2008/0135396 A1 | 6/2008 | Blum |
| 2008/0193989 A1 | 8/2008 | Verser et al. |
| 2008/0210540 A1 | 9/2008 | Dieterle |
| 2009/0014313 A1 | 1/2009 | Lee et al. |
| 2009/0023192 A1 | 1/2009 | Verser et al. |
| 2009/0081749 A1 | 3/2009 | Verser et al. |
| 2009/0166172 A1 | 7/2009 | Casey et al. |
| 2009/0318573 A1 | 12/2009 | Stites et al. |
| 2010/0029980 A1 | 2/2010 | Johnston et al. |
| 2010/0029995 A1 | 2/2010 | Johnston et al. |
| 2010/0121114 A1 | 5/2010 | Johnston et al. |
| 2011/0082322 A1 | 4/2011 | Jevtic et al. |
| 2011/0190532 A1 | 8/2011 | Johnston et al. |
| 2011/0190549 A1 | 8/2011 | Horton et al. |
| 2012/0010438 A1 | 1/2012 | Lee et al. |
| 2012/0010439 A1 | 1/2012 | Jevtic et al. |
| 2012/0010445 A1 | 1/2012 | Johnston et al. |
| 2012/0010447 A1 | 1/2012 | Warner et al. |

FOREIGN PATENT DOCUMENTS

| | | |
|---|---|---|
| EP | 0104197 | 4/1984 |
| EP | 0137749 | 4/1985 |
| EP | 0167300 | 1/1986 |
| EP | 0456647 | 11/1991 |
| EP | 1614458 | 1/2006 |
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| JP | 4-193304 | 7/1992 |
| WO | WO 83/03409 | 10/1983 |
| WO | WO 2008/135192 | 11/2008 |
| WO | WO 2009/009322 | 1/2009 |
| WO | WO 2009/009323 | 1/2009 |
| WO | WO 2009/048335 | 4/2009 |
| WO | WO 2009/063176 | 5/2009 |
| WO | WO 2010/055285 | 5/2010 |
| WO | WO 2011/097190 | 8/2011 |
| WO | WO 2011/097211 | 8/2011 |
| WO | WO 2011/097220 | 8/2011 |
| WO | WO 2011/097227 | 8/2011 |
| WO | WO 2011/140457 | 11/2011 |
| WO | WO 2012/006228 | 1/2012 |

OTHER PUBLICATIONS

ZeaChem, Inc., Technology Overview, Lakewood, Colorado www.zeachem.com, 2008.

Santori et al.(2000). Hydrogenation of carbonylic compounds on Pt/SiO2 catalysts modified with SnBu4, Studies in Surface Science and Catalysis, 130, 2063-2068.

Rachmady, Acetic Acid Reduction by H2 on Bimetallic Pt—Fe Catalysts, Journal of Catalysis 209, 87-98 (Apr. 1, 2002), Elsevier Science (USA).

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Hilmen, Separation of Azeotropic Mixtures: Tools for Analysis and Studies on Batch Distillation Operation (Nov. 2000) p. 17-20.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

Amit M. Goda et al., DFT modeling of selective reduction of acetic acid to acetaldehyde on Pt-based bimetallic catalysts, 20th NAM, Houston, TX, Jun. 17-22, 2007 available online at <http://www.nacatsoc.org/20nam/abstracts/O-S9-18.pdf>.

Alcala, et al., (2005). Experimental and DFT studies of the conversion of ethanol and acetic acid on PtSn-based catalysts, Journal of Physical Chemistry, 109(6), 2074-2085.

Huang et al., "Low-Energy Distillation-Membrane Separation Process," vol. 49, Jan. 3, 2010, pp. 3760-3768.

International Search Report and Written Opinion for PCT/US2011/042753 mailed on Dec. 5, 2011.

International Search Report and Written Opinion for PCT/US2012/035183 mailed Jun. 14, 2012.

International Written Opinion for PCT/US2011/042753 mailed Jul. 16, 2012.

Written Opinion mailed Jul. 16, 2012 in corresponding International Application No. PCT/US2011/042753.

International Search Report and Written Opinion mailed Aug. 21, 2012 in corresponding International Application No. PCT/US2012/035210.

International Preliminary Report on Patentability for PCT/US2011/042753 mailed Oct. 22, 2012.

RECOVERING ETHANOL SIDEDRAW BY SEPARATING CRUDE PRODUCT FROM HYDROGENATION PROCESS

CROSS REFERENCE TO RELATED APPLICATIONS

This application claims priority to U.S. Provisional App. No. 61/570,604, filed on Dec. 14, 2011, the entirety of which is incorporated herein by reference. This application also is continuation-in-part of U.S. patent application Ser. No. 13/094,537, filed Apr. 26, 2011, which claims priority to U.S. Provisional App. No. 61/363,109, filed on Jul. 9, 2010, the entirety of which is incorporated herein by reference.

FIELD OF THE INVENTION

The present invention relates generally to processes for recovering ethanol produced by hydrogenation acetic acid, ethyl acetate, and mixtures thereof.

BACKGROUND OF THE INVENTION

Ethanol for industrial use is conventionally produced from organic feed stocks, such as petroleum oil, natural gas, or coal, from feed stock intermediates, such as syngas, or from starchy materials or cellulose materials, such as corn or sugar cane. Conventional methods for producing ethanol from organic feed stocks, as well as from cellulose materials, include the acid-catalyzed hydration of ethylene, methanol homologation, direct alcohol synthesis, and Fischer-Tropsch synthesis. Instability in organic feed stock prices contributes to fluctuations in the cost of conventionally produced ethanol, making the need for alternative sources of ethanol production all the greater when feed stock prices rise. Starchy materials, as well as cellulosic materials, are converted to ethanol by fermentation. However, fermentation is typically used for consumer production of ethanol, which is suitable for fuels or human consumption. In addition, fermentation of starchy or cellulosic materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol product and a stream of acetic acid and ethyl acetate, which is recycled to the hydrogenation reactor.

U.S. Pat. No. 7,842,844 describes a process for improving selectivity and catalyst activity and operating life for the conversion of hydrocarbons to ethanol and optionally acetic acid in the presence of a particulate catalyst, said conversion proceeding via a syngas generation intermediate step.

The need remains for improved processes for recovering ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol comprising hydrogenating acetic acid in a reactor in the presence of a catalyst to form a crude ethanol product, separating at least a portion of the crude ethanol product in a first distillation column to yield a first residue comprising acetic acid and a first distillate comprising ethanol, ethyl acetate, and water, removing water from at least a portion of the first distillate to yield an ethanol mixture stream comprising less than 10 wt. % water, and separating a portion of the ethanol mixture stream in a second distillation column to yield an ethanol product sidedraw, either in the vapor or liquid phase, a second residue comprising water and a second distillate comprising ethyl acetate. In one embodiment, the ethanol product sidedraw is enriched in ethanol compared to the second residue. At least 40% of the ethanol in the ethanol mixture stream may be removed in the ethanol product sidedraw. The ethanol product sidedraw comprises less than 500 wppm acetic acid and less than 100 wppm ethyl acetate. The ethanol product sidedraw may be withdrawn below a feed location of the ethanol mixture stream to the second distillation column. In one embodiment, the ethanol product sidedraw is an industrial grade ethanol comprising less than 12 wt. % water. In some embodiments, the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

In a second embodiment, the present invention is directed to a process for producing ethanol comprising hydrogenating acetic acid in a reactor in the presence of a catalyst to form a crude ethanol product, separating at least a portion of the crude ethanol product in a first distillation column to yield a first residue comprising acetic acid and a first distillate comprising ethanol, ethyl acetate, and water, removing water from at least a portion of the first distillate to yield an ethanol mixture stream comprising less than 10 wt. % water, separating a portion of the ethanol mixture stream in a second distillation column to yield an ethanol product sidedraw, either in the vapor or liquid phase, a second residue comprising water and a second distillate comprising ethyl acetate, and reducing the water content of the ethanol product sidedraw to yield an ethanol product stream having a reduced water content. The ethanol product stream having a reduced water content may have less than 3 wt. % water. An adsorption unit or membrane may be used to reduce the water concentration. In one embodiment, the ethanol product stream having a reduced water content may be a fuel grade ethanol comprising less than 2 wt. % water.

In a third embodiment, the present invention is directed to a process for producing ethanol comprising hydrogenating acetic acid in a reactor in the presence of a catalyst to form a crude ethanol product, separating at least a portion of the crude ethanol product in a column into a first distillate comprising ethanol and a first residue comprising acetic acid and water, wherein a substantial portion of the water in the crude ethanol product that is fed to the column is removed in the first residue, and separating a portion of the ethanol mixture stream to the second distillation column to yield an ethanol product sidedraw, either in the vapor or liquid phase, a second residue comprising water and a second distillate comprising ethyl acetate. In one embodiment, the second residue may also comprise acetic acid.

BRIEF DESCRIPTION OF DRAWINGS

The invention is described in detail below with reference to the appended drawings, wherein like numerals designate similar parts.

DETAILED DESCRIPTION OF THE INVENTION

Figure 1A:
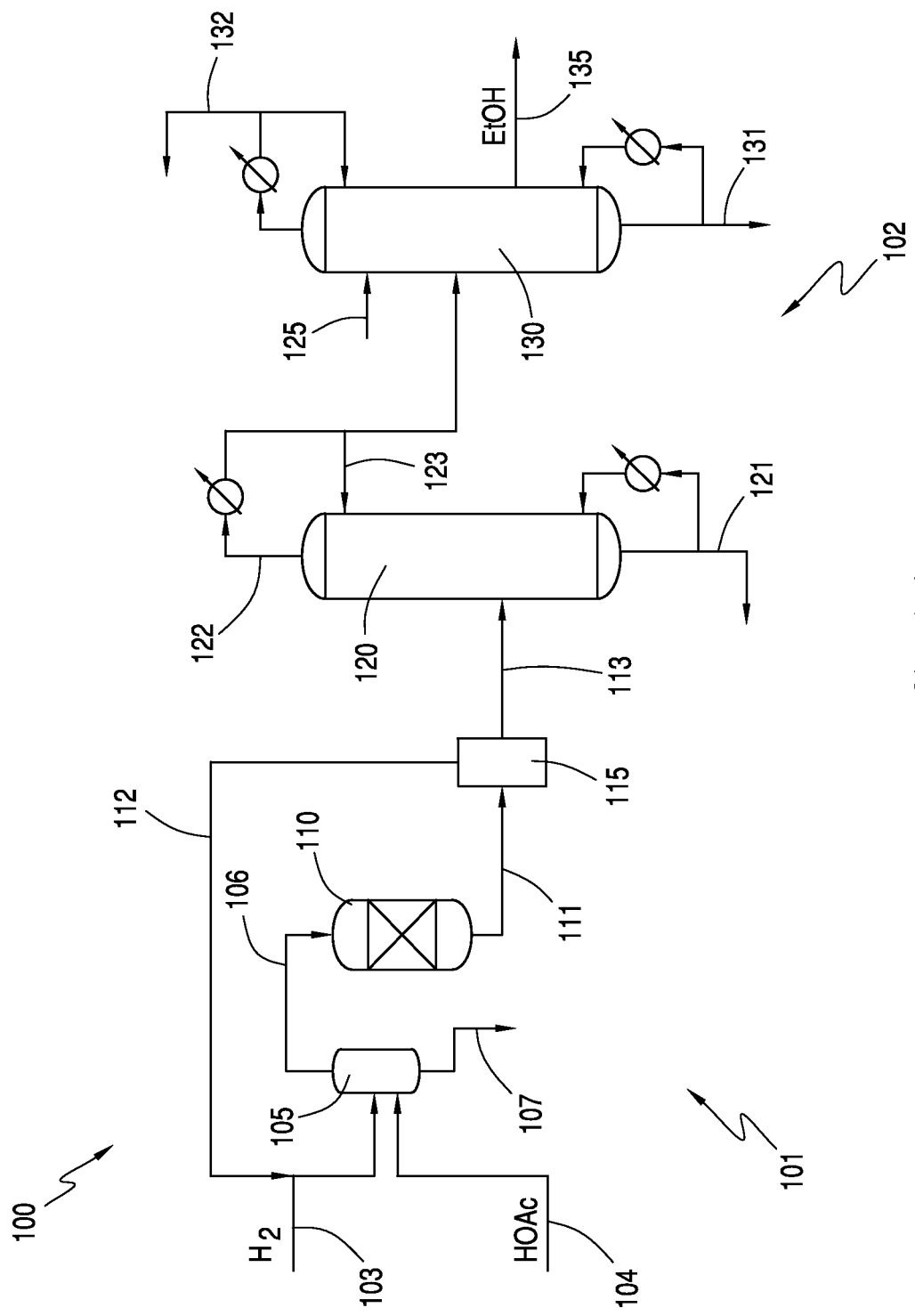
FIGS. 1A and 1B are schematic diagrams of a hydrogenation process and two column separation process in accordance with an embodiment of the present invention.

The present invention relates to processes for purifying ethanol produced by hydrogenating acetic acid in the presence of a catalyst. The hydrogenation reaction produces a crude ethanol product that comprises ethanol, water, acetic acid, and other impurities such as ethyl acetate, acetaldehyde, and diethyl acetal. In situ esterification of the ethanol and acetic acid in the crude ethanol product may produce additional ethyl acetate impurities. To efficiently remove these impurities, the processes of the present invention involve separating the crude ethanol product into a residue stream comprising water and unreacted acetic acid and a distillate stream comprising ethanol. The distillate is then separated in a second column to produce a second distillate comprising ethyl acetate, a second residue comprising water, and an ethanol product sidedraw. The ethanol product sidedraw may be withdrawn below a feed location to the second column. In one embodiment, although the second residue may also comprise ethanol, the ethanol product sidedraw is preferably enriched in ethanol compared to the second residue. The ethanol product sidedraw may be a vapor or liquid. Preferably, the ethanol product sidedraw is a vapor.

In recovering ethanol, the processes of the present invention use one or more distillation columns. Acetic acid is removed from the crude ethanol product in the residue stream of the initial (first) column to reduce esterification that would consume the desired ethanol product. In preferred embodiments, the first residue stream comprises a substantial portion of the water and the acetic acid from the crude ethanol product. In one embodiment, the initial column is operated so that minor amounts of, preferably no, acetic acid is carried over in the distillate and minor amounts of, preferably no, ethanol is leaked into the residue. The substantial portion of the water removed in the residue may vary depending on the composition of the crude ethanol product, which is a result of the acetic acid conversion and selectivity to ethanol. Removing less water in the residue may increase acetic acid carry over in the distillate. In addition, leaving too much water in the residue may also cause increases in ethanol leakage into the residue. Also, depending on the conversion, the energy requirement may also increase when too much water is left in the distillate.

In some embodiments, water is further removed from the first distillate stream before the first distillate stream is introduced to the second column. Advantageously, this separation approach reduces the energy requirements to recover ethanol from the crude ethanol product. Preferably, a majority of the water in the first distillate may be removed via a water removal unit to produce an ethanol mixture stream and a water stream. The ethanol mixture stream is then introduced to the second column. The water removal unit, such as an adsorption unit, membrane, extractive column distillation, molecular sieves, or a combination thereof may remove at least 90% of the water from the treated portion of the first distillate, and more preferably from 95% to 99.99%. The water stream may be combined with any other water stream from the system and preferably is removed from the system. The water stream may also comprise ethanol, in which case it may be desirable to feed all or a portion of the water stream back to the first column for further ethanol recovery. Optionally, at least a portion of the water stream is fed to the second column. More preferably, at least a portion of the first distillate is fed to the second column. Additional water introduced to the second column will act as an extractive distillation agent, further improving the efficiency of producing ethanol from the crude ethanol product. The water introduced to the second column may come from any stream comprising water produced in the current processes, or optionally from outside of the current processes.

The ethanol product sidedraw produced by the processes of the current invention is enriched in ethanol compared to the second residue. In one embodiment, at least 40% of the ethanol in the ethanol mixture stream and/or first distillate is removed in the ethanol product sidedraw, e.g., at least 50%, at least 60%, or at least 70%. Preferably, the ethanol product sidedraw also comprises less than 500 wppm acetic acid, e.g., less than 400 wppm, less than 300 wppm, or less than 250 wppm. Preferably, the ethanol product sidedraw comprises less than 100 wppm ethyl acetate, e.g., less than 90 wppm, or less than 75 wppm. In some embodiments, the ethanol product sidedraw is an industrial grade ethanol comprising less than 12 wt. % water. In one embodiment, the ethanol product sidedraw is withdrawn below the feed location of the ethanol mixture stream.

In some embodiments, the processes of the present invention further comprise the step of reducing the water content of the ethanol product sidedraw to yield an ethanol product stream having a reduced water content. In some embodiments, the reducing step uses an adsorption unit, membrane, molecular sieves, or a combination thereof. In one embodiment, the adsorption unit may be a pressure swing adsorption (PSA) unit. In an exemplary embodiment, at least a portion of the ethanol product sidedraw is separated with a membrane into a permeate stream comprising water and a retentate stream comprising ethanol. The retentate stream preferably has a lower water concentration than the ethanol product sidedraw. Preferably, the retentate stream comprises less than 3 wt. % water. Preferably, the retentate stream can be used as a fuel grade ethanol because the retentate stream may comprise less than 2 wt. % water, e.g. less than 0.5 wt. %.

The process of the present invention may be used with any hydrogenation process for producing ethanol. The materials, catalysts, reaction conditions, and separation processes that may be used in the hydrogenation of acetic acid are described further below.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from other carbon sources have drawn increasing interest. In particular, when petroleum is relatively expensive, it may become advantageous to produce acetic acid from synthesis gas ("syngas") that is derived from other available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from a variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Biomass-derived syngas has a detectable $^{14}C$ isotope content as compared to fossil fuels such as coal or natural gas. An equilibrium forms in the Earth's atmosphere between constant new formation and constant degradation, and so the proportion of the $^{14}C$ nuclei in the carbon in the atmosphere on Earth is constant over long periods. The same distribution ratio $n^{14}C:n^{12}C$ ratio is established in living organisms as is present in the surrounding atmosphere, which stops at death and $^{14}C$ decomposes at a half life of about 6000 years. Methanol, acetic acid and/or ethanol formed from biomass-derived syngas would be expected to have a $^{14}C$ content that is substantially similar to living organisms. For example, the $^{14}C:^{12}C$ ratio of the methanol, acetic acid and/or ethanol may be from one half to about 1 of the $^{14}C:^{12}C$ ratio for living organisms. In other embodiments, the syngas, methanol, acetic acid and/or ethanol described herein are derived wholly from fossil fuels, i.e. carbon sources produced over 60,000 years ago, may have no detectable $^{14}C$ content.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola*. Optionally, in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. No. 6,509,180, and U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. Another biomass source is black liquor, which is an aqueous solution of lignin residues, hemicellulose, and inorganic chemicals.

U.S. Pat. No. RE 35,377, also incorporated herein by reference, provides a method for the production of methanol by converting carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into syngas, and U.S. Pat. No. 6,685,754, which discloses a method for the production of a hydrogen-containing gas composition, such as a syngas including hydrogen and carbon monoxide, are incorporated herein by reference in their entireties.

Acetic acid fed to the hydrogenation reactor may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its aldehyde, may be beneficial in producing propanol. Water may also be present in the acetic acid feed.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system so that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 2100 kPa. The reactants may be fed to the reactor at a gas hourly space velocity (GHSV) from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds.

The hydrogenation of acetic acid to form ethanol is preferably conducted in the presence of a hydrogenation catalyst. Exemplary catalysts are further described in U.S. Pat. Nos. 7,608,744 and 7,863,489, and U.S. Pub. Nos. 2010/0121114 and 2010/0197985, the entireties of which are incorporated herein by reference. In another embodiment, the catalyst comprises a Co/Mo/S catalyst of the type described in U.S. Pub. No. 2009/0069609, the entirety of which is incorporated herein by reference. In some embodiments the first and second catalysts may be bulk catalysts.

In one embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel.

In certain embodiments where the catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 7.5 wt. %.

Preferred metal combinations for exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, or ruthenium/iron.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. When present, the total weight of the third metal preferably is from 0.05 to 20 wt. %, e.g., from 0.1 to 10 wt. %, or from 0.1 to 7.5 wt. %. In one embodiment, the catalyst may comprise platinum, tin and cobalt.

In addition to one or more metals, in some embodiments of the present invention the catalysts further comprise a support or a modified support. As used herein, the term "modified support" refers to a support that includes a support material and a support modifier, which adjusts the acidity of the support material. The total weight of the support or modified support, based on the total weight of the catalyst, preferably is from 75 to 99.9 wt. %, e.g., from 78 to 97 wt. %, or from 80 to 95 wt. %. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

The support may be a modified support and is present in an amount from 0.1 to 50 wt. %, from 0.2 to 25 wt. %, from 1 to 20 wt. %, or from 3 to 15 wt. %, based on the total weight of the catalyst. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, $Sb_2O_3$, $WO_3$, $MoO_3$, $Fe_2O_3$, $Cr_2O_3$, $V_2O_5$, $MnO_2$, $CuO$, $Co_2O_3$, and $Bi_2O_3$. Preferred support modifiers include oxides of tungsten, molybdenum, and vanadium.

In another embodiment, the support modifier may be a basic modifier that has a low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. The basic support modifier may be selected from the group consisting of oxides and metasilicates of any of sodium, potassium, magnesium, calcium, scandium, yttrium, and zinc, as well as mixtures of any of the foregoing. In one embodiment, the basic support modifier is a calcium silicate, such as calcium metasilicate ($CaSiO_3$). The calcium metasilicate may be crystalline or amorphous.

Catalysts on a modified support may include one or more metals selected from the group consisting of platinum, palladium, cobalt, tin, and rhenium on a silica support, optionally modified by one or more modifiers selected from the group consisting of calcium metasilicate, and one or more oxides of tungsten, molybdenum, and/or vanadium.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485 referred to above, the entireties of which are incorporated herein by reference.

After the washing, drying and calcining of the catalyst is completed, the catalyst may be reduced in order to activate the catalyst. Reduction is carried out in the presence of a reducing gas, preferably hydrogen. The reducing gas is continuously passed over the catalyst at an initial ambient temperature that is increased up to 400° C. In one embodiment, the reduction is preferably carried out after the catalyst has been loaded into the reaction vessel where the hydrogenation will be carried out.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a percentage based on acetic acid in the feed. The conversion may be at least 40%, e.g., at least 50%, at least 60%, at least 70% or at least 80%. Although catalysts that have high conversions are desirable, such as at least 80% or at least 90%, in some embodiments a low conversion may be acceptable at high selectivity for ethanol.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethanol is at least 60%, e.g., at least 70%, or at least 80%. Preferred embodiments of the hydrogenation process also have low selectivity to undesirable products, such as methane, ethane, and carbon dioxide. The selectivity to these undesirable products preferably is less than 4%, e.g., less than 2% or less than 1%.

The term "productivity," as used herein, refers to the grams of a specified product, e.g., ethanol, formed during the hydrogenation based on the kilograms of catalyst used per hour. The productivity may range from 100 to 3,000 grams of ethanol per kilogram of catalyst per hour.

In various embodiments of the present invention, the crude ethanol product produced by the hydrogenation process, before any subsequent processing, such as purification and separation, will typically comprise acetic acid, ethanol and water. Exemplary compositional ranges for the crude ethanol product are provided in Table 1, excluding hydrogen. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 72 | 15 to 72 | 15 to 70 | 25 to 65 |
| Acetic Acid | 0 to 90 | 0 to 50 | 0 to 35 | 0 to 15 |
| Water | 5 to 40 | 5 to 30 | 10 to 30 | 10 to 26 |
| Ethyl Acetate | 0 to 30 | 1 to 25 | 3 to 20 | 5 to 18 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product of Table 1 may have low concentrations of acetic acid with higher conversion, and in terms of ranges, the acetic acid concentration of Table 1 may range from 0.01 wt. % to 20 wt. %, e.g., 0.05 wt. % to 15 wt. %, from 0.1 wt. % to 10 wt. % or from 1 wt. % to 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

The columns shown in the figures may comprise any distillation column capable of performing the desired separation and/or purification. Each column preferably comprises a tray column having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns so that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

Exemplary ethanol recovery systems in accordance with embodiments of the present invention are shown in FIGS. 1A, 1B, 2A, 2B, 3A, and 3B. Each hydrogenation system 100 provides a suitable hydrogenation reactor and a process for separating ethanol from the crude reaction mixture according to an embodiment of the invention. System 100 comprises reaction zone 101 and separation zone 102. Reaction zone 101 comprises reactor 110, hydrogen feed line 103 and acetic acid feed line 104. Separation zone 102 comprises a separator 115, and distillation columns 120 and 130.

Hydrogenation system 100 includes reaction zone 101 and separation zone 102. Hydrogen and acetic acid via lines 103 and 104, respectively, are fed to a vaporizer 105 to create a vapor feed stream in line 106 that is directed to reactor 110 and a blowdown stream 107. In one embodiment, lines 103 and 104 may be combined and jointly fed to vaporizer 105. The temperature of the vapor feed stream in line 106 is preferably from 100° C. to 350° C., e.g., from 120° C. to 310° C. or from 150° C. to 300° C. Any feed that is not vaporized is removed from vaporizer 105 via blowdown stream 107. In addition, although line 106 is shown as being directed to the top of reactor 110, line 106 may be directed to the side, upper portion, or bottom of reactor 110.

Reactor 110 contains the catalyst that is used in the hydrogenation of the carboxylic acid, preferably acetic acid. In one embodiment, one or more guard beds (not shown) may be used upstream of the reactor, optionally upstream of vaporizer 105, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens. During the hydrogenation process, a crude ethanol product is withdrawn, preferably continuously, from reactor 110 via line 111.

The crude ethanol product in line 111 may be condensed and fed to a separator 115, which, in turn, provides a vapor stream 112 and a liquid stream 113. In some embodiments, separator 115 may comprise a flasher or a knockout pot. The separator 115 may operate at a temperature from 20° C. to 250° C., e.g., from 30° C. to 225° C. or from 60° C. to 200° C. The pressure of separator 115 may be from 50 kPa to 2500 kPa, e.g., from 75 kPa to 2250 kPa or from 100 kPa to 2100 kPa. Optionally, the crude ethanol product in line 111 may pass through one or more membranes to separate hydrogen and/or other non-condensable gases.

Vapor stream 112 exiting separator 115 may comprise hydrogen and hydrocarbons, and may be purged and/or returned to reaction zone 101. When returned to reaction zone 101, vapor stream 112 is combined with the hydrogen feed 103 and co-fed to vaporizer 105. In some embodiments, the returned vapor stream 112 may be compressed before being combined with hydrogen feed 103.

The liquid stream 113 from separator 115 is withdrawn and directed as a feed composition to the side of first distillation column 120, also referred to as an "acid separation column." In one embodiment, the contents of liquid stream 113 are substantially similar to the crude ethanol product obtained from the reactor, except that the composition has been depleted of hydrogen, carbon dioxide, methane and/or ethane, which are removed by separator 115. Accordingly, liquid stream 113 may also be referred to as a crude ethanol product. Exemplary components of liquid stream 113 are provided in Table 2. It should be understood that liquid stream 113 may contain other components, not listed in Table 2.

TABLE 2

FEED COMPOSITION TO COLUMN 120
(Liquid Stream 113)

|  | Conc. (wt. %) | Conc. (wt. %) | Conc. (wt. %) |
|---|---|---|---|
| Ethanol | 5 to 72 | 10 to 70 | 15 to 65 |
| Acetic Acid | <90 | 0.01 to 20 | 0.05 to 15 |
| Water | 5 to 40 | 5 to 30 | 10 to 26 |
| Ethyl Acetate | <30 | 1 to 25 | 3 to 20 |
| Acetaldehyde | <10 | 0.001 to 3 | 0.1 to 3 |
| Acetal | <5 | 0.01 to 5 | 0.01 to 3 |
| Acetone | <5 | 0.0005 to 0.05 | 0.001 to 0.03 |

The amounts indicated as less than (<) in the tables throughout the present specification are preferably not present and if present may be present in amounts greater than 0.0001 wt. %.

In one preferred embodiment, reaction zone 101 operates at above 80% acetic acid conversion, e.g., above 90% conversion or above 99% conversion. Thus, the acetic acid concentration in liquid stream 113 may be low.

Liquid stream 113 is introduced in the middle or lower portion of a first column 120, also referred to as acid-water column. For purposes of convenience, the columns in each exemplary separation process, may be referred as the first, second, third, etc., columns. In one embodiment, no entrainers are added to first column 120. In first column 120, water and unreacted acetic acid, along with any other heavy components, if present, are removed from liquid stream 113 and are withdrawn, preferably continuously, as a first residue in line 121. Preferably, a substantial portion of the water in the crude ethanol product that is fed to first column 120 may be removed in the first residue, for example, up to about 75% or to about 90% of the water from the crude ethanol product. First column 120 also forms a first distillate, which is withdrawn in line 122. A portion of the first distillate may be returned to first column 120 via line 123.

When column 120 is operated under about 170 kPa, the temperature of the residue exiting in line 121 preferably is from 90° C. to 130° C., e.g., from 95° C. to 120° C. or from 100° C. to 115° C. The temperature of the distillate exiting in line 122 preferably is from 60° C. to 90° C., e.g., from 65° C. to 85° C. or from 70° C. to 80° C. In some embodiments, the pressure of first column 120 may range from 0.1 kPa to 510 kPa, e.g., from 1 kPa to 475 kPa or from 1 kPa to 375 kPa.

Some of the residues withdrawn from the separation zone 102 comprise acetic acid and water. Depending on the amount of water and acetic acid contained in the residue of first column 120, the residue may be treated in one or more of the following processes. The following are exemplary processes for further treating the residue and it should be understood that any of the following may be used regardless of acetic acid concentration. When the residue comprises a majority of acetic acid, e.g., greater than 70 wt. %, the residue may be recycled to the reactor without any separation of the water. In one embodiment, the residue may be separated into an acetic acid stream and a water stream when the residue comprises a majority of acetic acid, e.g., greater than 50 wt. %. Acetic acid may also be recovered in some embodiments from the residue having a lower acetic acid concentration. The residue may be separated into the acetic acid and water streams by a distillation column or one or more membranes. If a membrane or an array of membranes is employed to separate the acetic acid from the water, the membrane or array of membranes may be selected from any suitable acid resistant membrane that is capable of removing a permeate water stream. The resulting acetic acid stream optionally is returned to the reactor 110. The resulting water stream may be used as an extractive agent or to hydrolyze an ester-containing stream in a hydrolysis unit.

In other embodiments, for example, where the residue comprises less than 50 wt. % acetic acid, possible options include one or more of: (i) returning a portion of the residue to reactor 108, (ii) neutralizing the acetic acid, (iii) reacting the acetic acid with an alcohol, or (iv) disposing of the residue in a waste water treatment facility. It also may be possible to separate a residue comprising less than 50 wt. % acetic acid using a weak acid recovery distillation column to which a solvent (optionally acting as an azeotroping agent) may be added. Exemplary solvents that may be suitable for this purpose include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. When neutralizing the acetic acid, it is preferred that the residue comprises less than 10 wt. % acetic acid. Acetic acid may be neutralized with any suitable alkali or alkaline earth metal base, such as sodium hydroxide or potassium hydroxide. When reacting acetic acid with an alcohol, it is preferred that the residue comprises less than 50 wt. % acetic acid. The alcohol may be any suitable alcohol, such as methanol, ethanol, propanol, butanol, or mixtures thereof. The reaction forms an ester that may be integrated with other systems, such as carbonylation production or an ester production process. Preferably, the alcohol comprises ethanol and the resulting ester comprises ethyl acetate. Optionally, the resulting ester may be fed to the hydrogenation reactor.

In some embodiments, when the residue comprises very minor amounts of acetic acid, e.g., less than 5 wt. %, the residue may be disposed of to a waste water treatment facility without further processing. The organic content, e.g., acetic acid content, of the residue beneficially may be suitable to feed microorganisms used in a waste water treatment facility.

The first distillate in line 122 comprises water, in addition to ethanol and other organics. In terms of ranges, the concentration of water in the first distillate in line 122 preferably is from 4 wt. % to 38 wt. %, e.g., from 7 wt. % to 32 wt. %, or from 7 to 25 wt. %. A portion of first distillate in line 122 may be condensed and refluxed, for example, at a ratio of from 10:1 to 1:10, e.g., from 3:1 to 1:3 or from 1:2 to 2:1. It is understood that reflux ratios may vary with the number of stages, feed locations, column efficiency and/or feed composition. Operating with a reflux ratio of greater than 3:1 may be less preferred because more energy may be required to operate the first column 120. The condensed portion of the first distillate may also be fed to a second column 130.

Figure 2A:
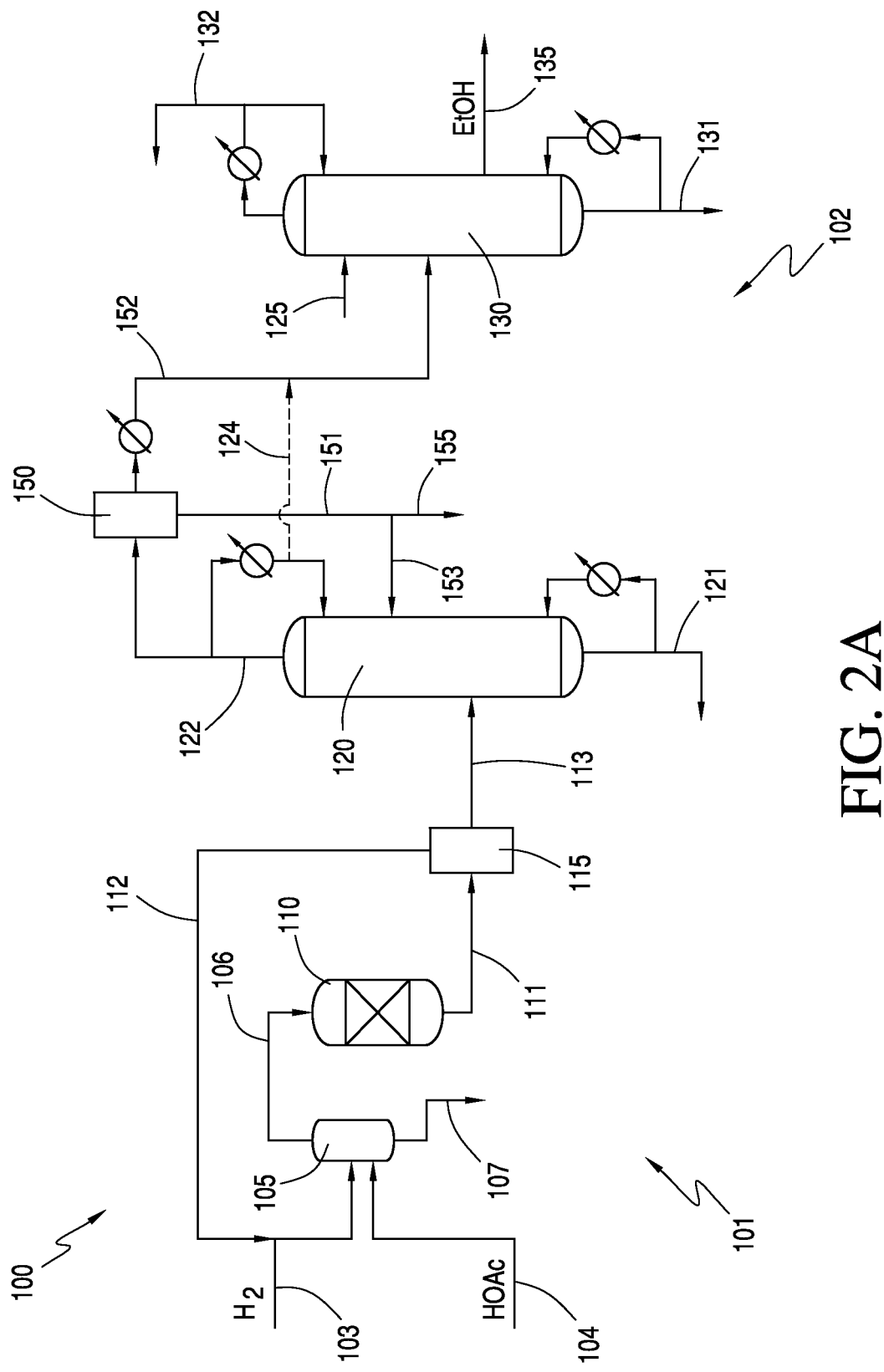
FIGS. 2A and 2B are schematic diagrams of another hydrogenation process and two column separation process having an intervening water separator to remove water in accordance with an embodiment of the present invention.
Figure 2B:
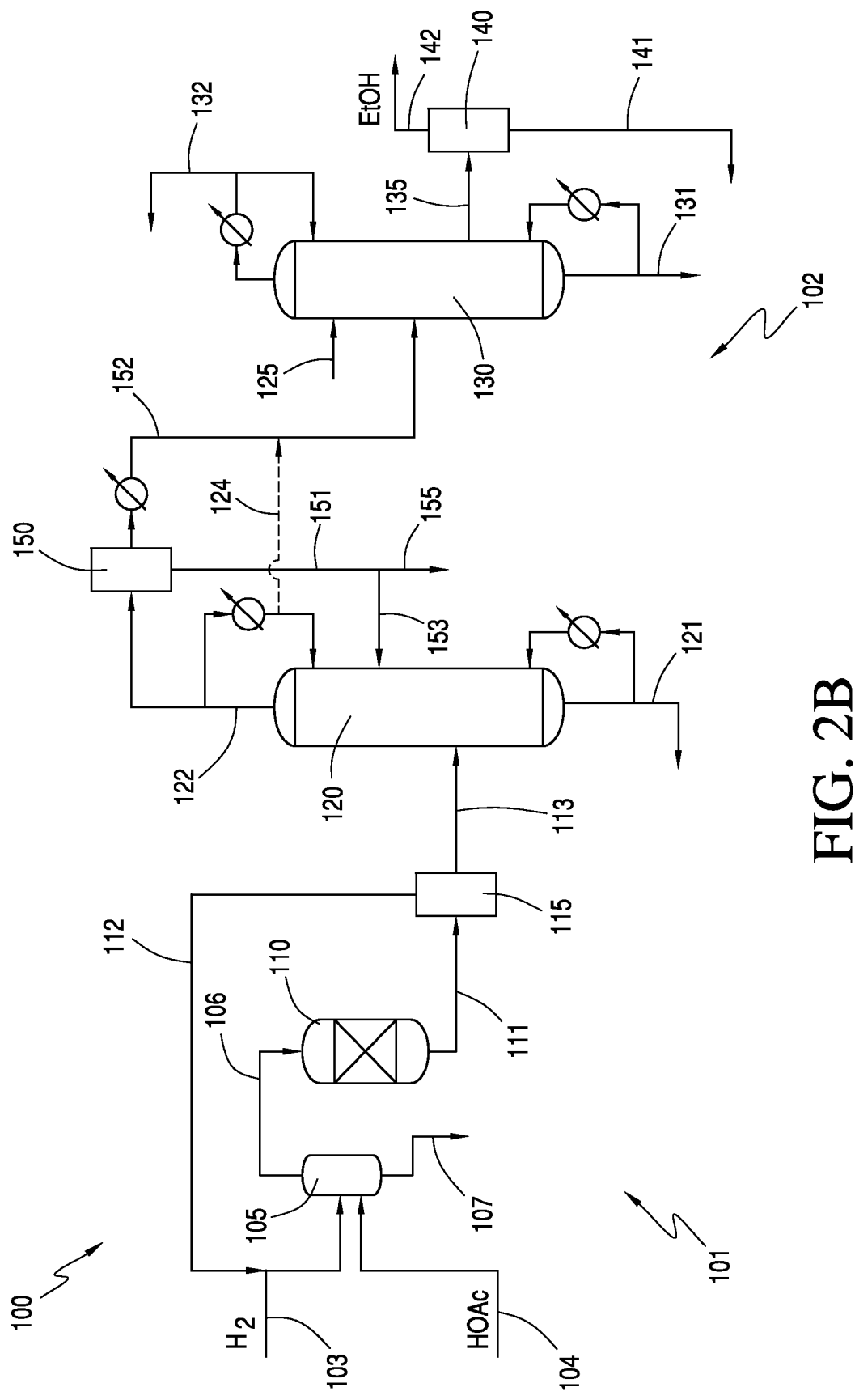

In FIGS. 2A and 2B, at least a portion of the first distillate in 122 is fed to a water separation unit 150. Water separation unit 150 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate. Water separator 150 may remove at least 95% of the water from the portion of first distillate in line 122, and more preferably from 99% to 99.99% of the water from the first distillate, in a water stream 151. All or a portion of water stream 151 may be returned to column 120 in line 153, where the water preferably is ultimately recovered from column 120 in the first residue in line 121. Additionally or alternatively, all or a portion of water stream 151 may be purged via line 155. The remaining portion of first distillate exits the water separator 150 as ethanol mixture stream 152. Ethanol mixture stream 152 may have a low concentration of water of less than 10 wt. %, e.g., less than 6 wt. % or less than 2 wt. %.

Figure 3A:
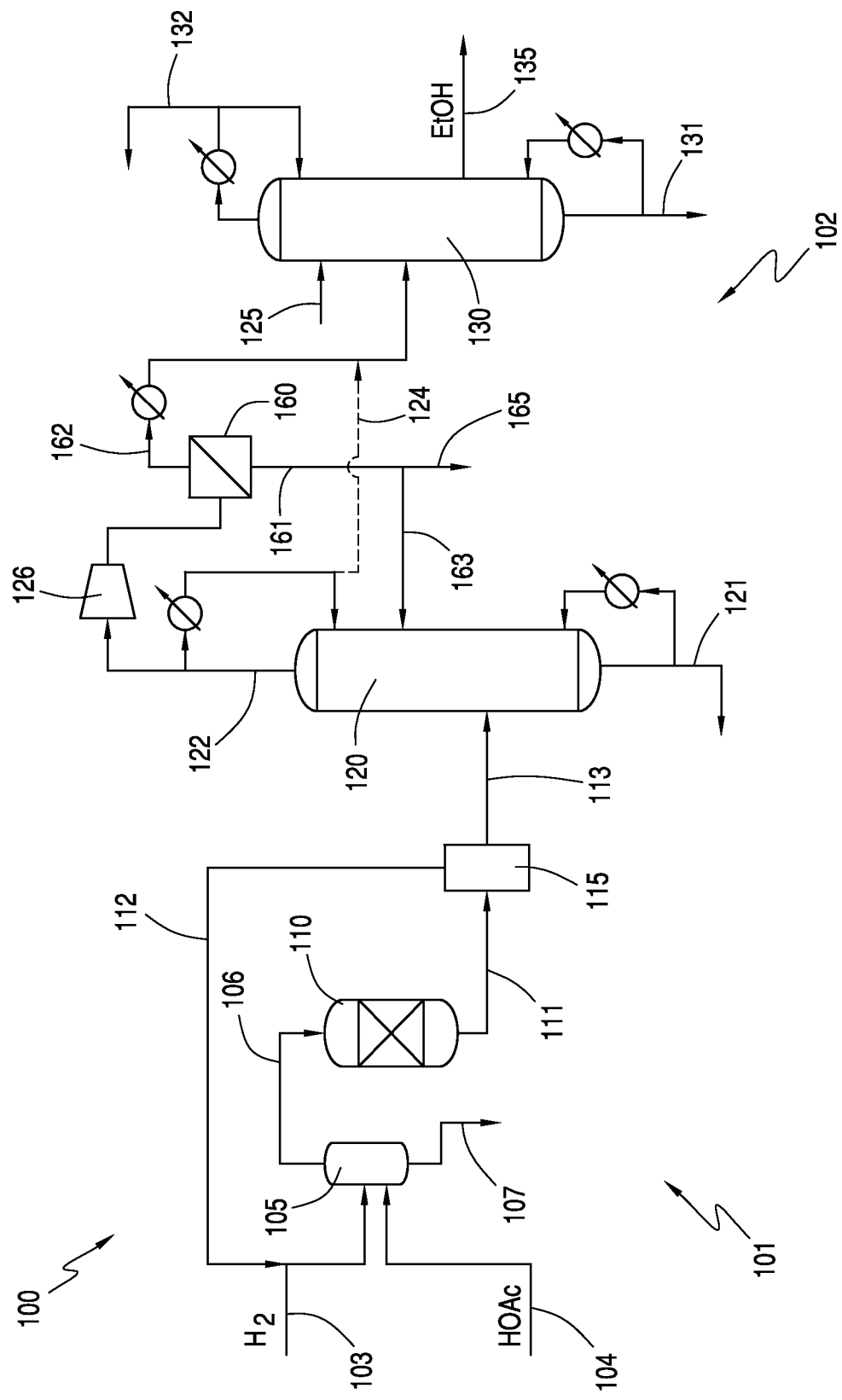
FIGS. 3A and 3B are schematic diagrams of another hydrogenation process and two column separation process having an intervening membrane to remove water in accordance with an embodiment of the present invention.
Figure 3B:
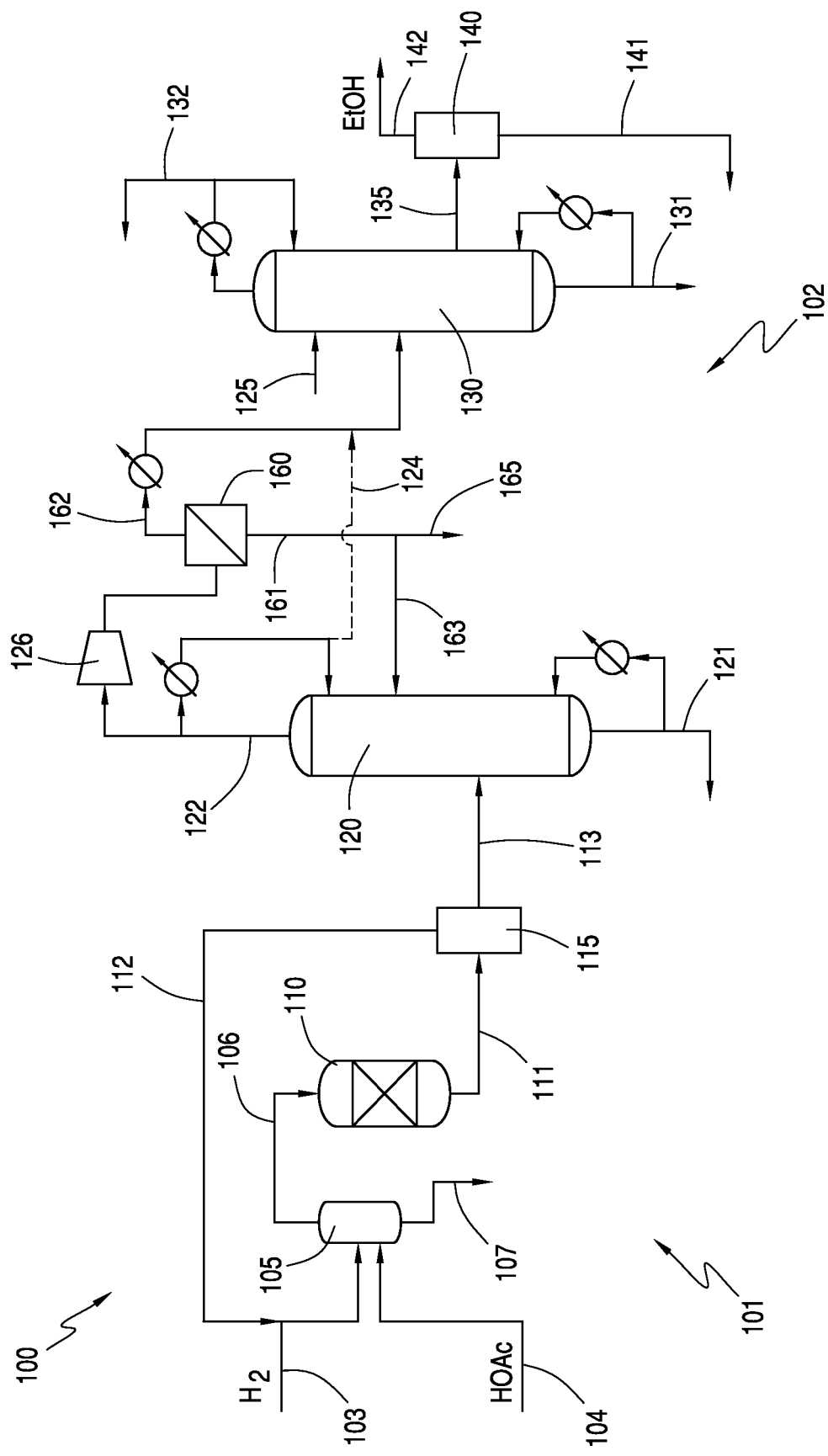

In the embodiments show in FIGS. 3A and 3B, water separator 160 is a pressure swing adsorption (PSA) unit. PSA unit 160 is optionally operated at a temperature from 30° C. to 160° C., e.g., from 80° C. to 140° C., and a pressure of from 0.01 kPa to 550 kPa, e.g., from 1 kPa to 150 kPa. PSA unit 160 may comprise two to five beds. PSA unit 160 may remove at least 95% of the water from the portion of first distillate in line 122, and more preferably from 95% to 99.99% of the water from the first distillate, in a water stream 161. All or a portion of water stream 161 may be returned to column 120 in line 163, where the water preferably is ultimately recovered from column 120 in the first residue in line 121. Additionally or alternatively, all or a portion of water stream 161 may be purged via line 165. The remaining portion of first distillate exits PSA unit 160 as ethanol mixture stream 162. Ethanol mixture stream 160 may have a low concentration of water of less than 10 wt. %, e.g., less than 6 wt. % or less than 2 wt. %. Exemplary components of ethanol mixture stream 152/162 and first residue in line 121 are provided in Table 3 below. It should also be understood that these streams may also contain other components, not listed, such as components derived from the feed.

TABLE 3

FIRST COLUMN 120 WITH WATER SEPARATION

| | Conc. (wt. %) | Conc. (wt. %) | Conc. (wt. %) |
|---|---|---|---|
| Ethanol Mixture Stream | | | |
| Ethanol | 20 to 95 | 30 to 95 | 40 to 95 |
| Water | <10 | 0.01 to 6 | 0.1 to 2 |
| Acetic Acid | <2 | 0.001 to 0.5 | 0.01 to 0.2 |
| Ethyl Acetate | <60 | 1 to 55 | 5 to 55 |
| Acetaldehyde | <10 | 0.001 to 5 | 0.01 to 4 |
| Acetal | <0.1 | <0.1 | <0.05 |
| Acetone | <0.05 | 0.001 to 0.03 | 0.01 to 0.025 |
| Residue | | | |
| Acetic Acid | <90 | 1 to 50 | 2 to 35 |
| Water | 30 to 100 | 45 to 95 | 60 to 90 |
| Ethanol | <1 | <0.9 | <0.3 |

Referring to FIGS. 2A, 2B, 3A and 3B, preferably, ethanol mixture stream 152/162 is not returned or refluxed to first column 120. The condensed portion of the first distillate in line 124 may be combined with ethanol mixture stream 152 or 162 to control the water concentration fed to second column 130. For example, in some embodiments the first distillate may be split into equal portions, while in other embodiments, all of the first distillate may be condensed or all of the first distillate may be processed in the water separation unit. In FIGS. 2A and 2B, the condensed portion in line 124 and ethanol mixture stream 152 are co-fed to second column 130. In other embodiments, the condensed portion in line 124 and ethanol mixture stream 152 may be separately fed to second column 130. In FIGS. 3A and 3B, the condensed portion in line 124 and ethanol mixture stream 162 are co-fed to second column 130. In other embodiments, the condensed portion in line 124 and ethanol mixture stream 162 may be separately fed to second column 130. The combined distillate and ethanol mixture has a total water concentration of greater than 0.5 wt. %, e.g., greater than 2 wt. % or greater than 5 wt. %. In terms of ranges, the total water concentration of the combined distillate and ethanol mixture may be from 0.5 to 15 wt. %, e.g., from 2 to 12 wt. %, or from 5 to 10 wt. %.

Second column 130, also referred to as the "light ends column," removes ethyl acetate and acetaldehyde from the first distillate in line 122 and/or ethanol mixture stream 152 or 162. Ethyl acetate and acetaldehyde are removed as a second distillate in line 132 and water is removed as the second residue in line 131. The ethanol product sidedraw is removed via line 135 as a vapor or liquid, preferably as a vapor sidedraw. Second column 130 may be a tray column or packed column. In one embodiment, second column 130 is a tray column having from 5 to 70 trays, e.g., from 15 to 50 trays or from 20 to 45 trays.

Second column 130 operates at a pressure ranging from 0.1 kPa to 510 kPa, e.g., from 10 kPa to 450 kPa or from 50 kPa to 350 kPa. Although the temperature of second column 130 may vary, when at about 20 kPa to 70 kPa, the temperature of the second residue exiting in line 131 preferably is from 30° C. to 75° C., e.g., from 35° C. to 70° C. or from 40° C. to 65° C. The temperature of the second distillate exiting in line 132 preferably is from 20° C. to 55° C., e.g., from 25° C. to 50° C. or from 30° C. to 45° C.

Optionally, water may be fed to second column 130 via line 125. The total concentration of water fed to second column 130 preferably is less than 10 wt. %. When first distillate in line 122 and/or ethanol mixture stream in line 152 or 162 comprises minor amounts of water, e.g., less than 1 wt. % or less than 0.5 wt. %, additional water may be fed to the second column 130 as an extractive agent in the upper portion of the column. A sufficient amount of water is preferably added via the extractive agent so that the total concentration of water fed to second column 130 is from 1 to 10 wt. % water, e.g., from 2 to 6 wt. %, based on the total weight of all components fed to second column 130. If the extractive agent comprises water, the water may be obtained from an external source or from an internal return/recycle line from one or more of the other columns or water separators.

Suitable extractive agents may also include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N'-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof. When extractive agents are used, a suitable recovery system, such as a further distillation column, may be used to recycle the extractive agent.

Exemplary components for the second distillate, ethanol sidedraw, and second residue compositions for the second column 130 are provided in Table 4, below. It should be understood that the distillate and residue may also contain other components, not listed in Table 4.

TABLE 4

| SECOND COLUMN 130 | | | |
|---|---|---|---|
| | Conc. (wt. %) | Conc. (wt. %) | Conc. (wt. %) |
| Second Distillate | | | |
| Ethyl Acetate | 5 to 90 | 10 to 80 | 15 to 75 |
| Acetaldehyde | <60 | 1 to 40 | 1 to 35 |
| Ethanol | <45 | 0.001 to 40 | 0.01 to 35 |
| Water | <20 | 0.01 to 10 | 0.1 to 5 |
| Ethanol Sidedraw | | | |
| Ethanol | 80 to 99.5 | 85 to 97 | 60 to 95 |
| Water | <20 | 0.001 to 15 | 0.01 to 10 |
| Ethyl Acetate | <1 | 0.001 to 0.5 | 0.001 to 0.01 |
| Acetic Acid | <0.05 | <0.01 | 0.001 to 0.01 |
| Second Residue | | | |
| Ethanol | 5 to 80 | 10 to 75 | 20 to 70 |
| Water | 5 to 80 | 10 to 75 | 20 to 70 |
| Ethyl Acetate | <1 | 0.001 to 2 | 0.001 to 0.5 |
| Acetic Acid | <2 | <1 | 0.001 to 1 |

In one embodiment, the ethanol sidedraw, as either a vapor or a liquid, may contain substantially no ethyl acetate or acetaldehyde. The second residue may be enriched in water with respect to the ethanol sidedraw. In addition, any acetic acid carried over from the first column may concentrate in the second residue.

The second distillate in line 132, which comprises ethyl acetate and/or acetaldehyde, preferably is refluxed, for example, at a reflux ratio of from 1:30 to 30:1, e.g., from 1:10 to 10:1 or from 1:3 to 3:1. Higher reflux ratios may be used as necessary. In one aspect, not shown, the second distillate in line 132 or a portion thereof may be returned to reactor 110. The ethyl acetate and/or acetaldehyde in the second distillate may be further reacted in hydrogenation reactor 110.

In one embodiment, the second distillate in line 132 may be further separated to produce an acetaldehyde-containing stream and an ethyl acetate-containing stream. This may allow a portion of either the resulting acetaldehyde-containing stream or ethyl acetate-containing stream to be recycled to reactor 110 while purging the other stream. The purge stream may be valuable as a source of either ethyl acetate and/or acetaldehyde.

In some embodiments, the second residue in line 131 may be further separated to recover ethanol or used as an ethanol solvent.

The ethanol product sidedraw in line 135 may be withdrawn below the feed location of the first distillate 122 and/or the ethanol mixture stream 152 or 162. Preferably, at least 40% of the ethanol in the ethanol mixture stream is removed in the ethanol product sidedraw, e.g., at least 50%, at least 60% or at least 70%. The ethanol product sidedraw 135 may be enriched in ethanol compared to the second residue 131. The ethanol product sidedraw 135 produced by the process of the present invention may be an industrial grade ethanol comprising from 75 to 96 wt. % ethanol, e.g., from 80 to 96 wt. % or from 85 to 96 wt. % ethanol, based on the total weight of the ethanol product. Preferably, the ethanol product sidedraw also comprises less than 500 wppm acetic acid, e.g., less than 400 wppm, less than 300 wppm, or less than 250 wppm. Preferably, the ethanol product sidedraw comprises less than 100 wppm ethyl acetate, e.g., less than 90 wppm, or less than 75 wppm. Exemplary ethanol product sidedraw compositional ranges are provided below in Table 5.

TABLE 5

ETHANOL PRODUCT COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The ethanol product sidedraw 135 composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the ethanol product sidedraw composition is from 80 to 1,000 wppm, e.g., from 95 to 1,000 wppm, from 100 to 700 wppm, or from 150 to 500 wppm. In one embodiment, the ethanol product sidedraw composition is substantially free of acetaldehyde, optionally comprising less than 8 wppm acetaldehyde, e.g., less than 5 wppm or less than 1 wppm.

Figure 1B:
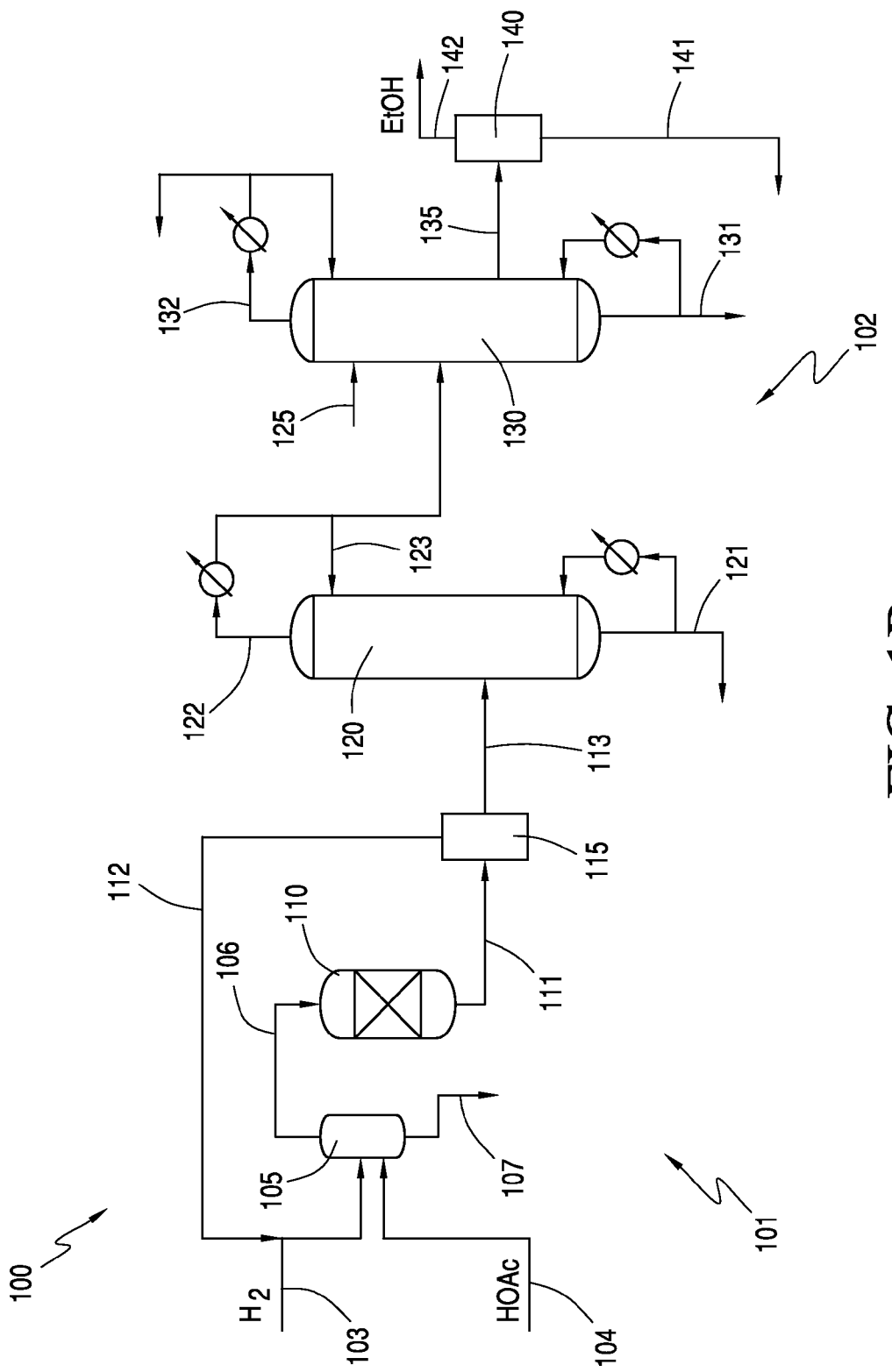

As shown in FIGS. 1B, 2B and 3B, further water separation may be used to yield an ethanol products stream. Ethanol product sidedraw 135 may be introduced to water separator 140. Water separation unit 140 may be an adsorption unit, membrane, molecular sieves, extractive column distillation, or a combination thereof. A membrane or an array of membranes may also be employed to separate water from the distillate. The membrane or array of membranes may be selected from any suitable membrane that is capable of removing a permeate water stream from a stream that also comprises ethanol and ethyl acetate. Water separator 140 may remove at least 90% of the water from the ethanol product sidedraw in line 135, and more preferably from 95% to 99.99% of the water from the ethanol product sidedraw 135, in a water stream 141. All or a portion of water stream 141 may be purged from the system or may be returned in whole or in part to second column 130 and removed in the second residue in line 131. The remaining portion of the ethanol product sidedraw exits the water separator 140 as ethanol product stream 142. In such embodiments, the ethanol concentration of the ethanol product stream may be higher than indicated in Table 5, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The ethanol produced by the embodiments of the present invention may be used in a variety of applications including applications as fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst, such as a zeolite catalyst, can be employed to dehydrate ethanol.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising:
hydrogenating acetic acid in a reactor in the presence of a catalyst to form a crude ethanol product;
separating at least a portion of the crude ethanol product in a first distillation column to yield a first residue comprising acetic acid and a first distillate comprising ethanol, ethyl acetate, and water;
removing water from at least a portion of the first distillate to yield an ethanol mixture stream comprising less than 10 wt. % water; and
separating a portion of the ethanol mixture stream in a second distillation column to yield an ethanol product sidedraw, a second residue comprising water and a second distillate comprising ethyl acetate.

2. The process of claim 1, wherein the ethanol product sidedraw is enriched in ethanol compared to the second residue.

3. The process of claim 1, further comprising reducing the water content of the ethanol product sidedraw to yield an ethanol product stream having a reduced water content.

4. The process of claim 3, wherein the reducing step uses an adsorption unit.

5. The process of claim 3, wherein the reducing step comprises separating at least a portion of the ethanol product sidedraw with a membrane into a permeate stream comprising water and a retentate stream comprising ethanol and having a lower water concentration than the ethanol product sidedraw.

6. The process of claim 5, wherein the retentate stream comprises less than 3 wt. % water.

7. The process of claim 5, wherein the retentate stream is a fuel grade ethanol comprising less than 2 wt. % water.

8. The process of claim 1, wherein at least 40% of the ethanol in the ethanol mixture stream is removed in the ethanol product sidedraw.

9. The process of claim 8, wherein the ethanol product sidedraw comprises less than 500 wppm acetic acid and less than 100 wppm ethyl acetate.

10. The process of claim 1, wherein the ethanol product sidedraw is withdrawn below a feed location of the ethanol mixture stream to the second distillation column.

11. The process of claim 1, wherein the ethanol product sidedraw is an industrial grade ethanol comprising less than 12 wt. % water.

12. A process for producing ethanol, comprising:
hydrogenating acetic acid in a reactor in the presence of a catalyst to form a crude ethanol product;
separating at least a portion of the crude ethanol product in a column into a first distillate comprising ethanol and a first residue comprising acetic acid and water, wherein a substantial portion of the water in the crude ethanol product that is fed to the column is removed in the first residue; and
separating a portion of the first distillate in the second distillation column to yield an ethanol product sidedraw, a second residue comprising water and a second distillate comprising ethyl acetate.

13. The process of claim 12, wherein the second residue further comprises acetic acid.

14. The process of claim 12, wherein the ethanol product sidedraw is enriched in ethanol compared to the second residue.

15. The process of claim 12, further comprising reducing the water content of the ethanol product sidedraw to yield an ethanol product stream having a reduced water content.

16. The process of claim 15, wherein reducing the water content uses an adsorption unit.

17. The process of claim 15, wherein the reducing step comprises separating at least a portion of the ethanol product sidedraw with a membrane into a permeate stream comprising water and a retentate stream comprising ethanol and having a lower water concentration than the ethanol product sidedraw.

18. The process of claim 17, wherein the retentate stream comprises less than 3 wt. % water.

19. The process of claim 17, wherein the retentate stream is a fuel grade ethanol comprising less than 2 wt. % water.

20. The process of claim 12, wherein at least 40% of the ethanol in the first distillate is removed in the ethanol product sidedraw.

21. The process of claim 12, wherein the ethanol product sidedraw comprises less than 500 wppm acetic acid and less than 100 wppm ethyl acetate.

22. The process of claim 12, wherein the ethanol product sidedraw is withdrawn below a feed location of the first distillate to the second distillation column.

23. The process of claim 12, wherein the ethanol product sidedraw is an industrial grade ethanol comprising less than 12 wt. % water.

* * * * *